United States Patent [19]

Shigeyasu et al.

[11] 4,327,226
[45] Apr. 27, 1982

[54] PROCESS AND APPARATUS FOR PRODUCING AROMATIC DICARBOXYLIC ACIDS

[75] Inventors: Motoo Shigeyasu; Takehiko Kitamura, both of Matsuyama, Japan

[73] Assignee: Matsuyama Petrochemicals Inc., Osaka, Japan

[21] Appl. No.: 171,510

[22] Filed: Jul. 23, 1980

Related U.S. Application Data

[60] Division of Ser. No. 958,918, Nov. 8, 1978, abandoned, which is a continuation of Ser. No. 771,493, Feb. 24, 1977, Pat. No. 4,159,493.

[30] Foreign Application Priority Data

Feb. 24, 1976 [JP] Japan .................................. 51/18422
Feb. 24, 1976 [JP] Japan .................................. 51/18423

[51] Int. Cl.³ ................................................ C07C 51/16
[52] U.S. Cl. .................................. 562/416; 562/412; 562/421; 562/422
[58] Field of Search ................ 562/412, 422, 421, 416

[56] References Cited

U.S. PATENT DOCUMENTS

| | | | |
|---|---|---|---|
| 3,093,626 | 6/1963 | Cines | 23/288 |
| 3,407,179 | 10/1968 | Carr | 23/285 |
| 3,677,714 | 7/1972 | Ledgett | 23/285 |
| 3,721,530 | 3/1973 | Bouchet | 23/288 |
| 4,062,654 | 12/1977 | Shigeyasu | 23/285 |

*Primary Examiner*—Alan Siegel
*Attorney, Agent, or Firm*—Sughrue, Mion, Zinn, Macpeak and Seas

[57] ABSTRACT

A process and an apparatus for producing an aromatic dicarboxylic acid by oxidizing a benzene derivative with molecular oxygen in the liquid phase in a lower aliphatic carboxylic acid as a solvent in the presence of an oxidation catalyst, wherein a starting material liquid e.g., a benzene derivative or a solution thereof in the lower aliphatic carboxylic acid, is fed into the liquid-phase reaction system in a uniformly dispersed state by being passed through a porous material causing the pressure of the starting material liquid just after passing through said porous material to drop more than about 1 $kg/m^2$ in relation to the pressure of the starting material liquid just before passing through said porous material. The resultant aromatic dicarboxylic acid has high purity and has good color.

31 Claims, 5 Drawing Figures

PROCESS AND APPARATUS FOR PRODUCING AROMATIC DICARBOXYLIC ACIDS

This is a division of application Ser. No. 958,918, filed Nov. 8, 1978, now abandoned, which is a continuation of application Ser. No. 771,493, filed Feb. 24, 1977, now U.S. Pat. No. 4,159,493.

BACKGROUND OF THE INVENTION

1. Field of the Invention

This invention relates to a process for producing an aromatic dicarboxylic acid, such as terephthalic acid, isophthalic acid or phthalic acid of high purity by a liquid-phase oxidation of a benzene derivative, such as xylene, diisopropyl benzene, diethyl benzene or cymene, with a molecular oxygen containing gas in a lower aliphatic carboxylic acid as a solvent in the presence of an oxidation catalyst; and to an apparatus for use in this process.

2. Description of the Prior Art

An aromatic dicarboxylic acid, particularly terephthalic acid, has been used in great quantities in recent years in the manufacture of polyesters by direct polymerization with ethylene glycol. As direct polymerization techniques have advanced, the requirements as to the quality of terephthalic acid have become more severe, and terephthalic acid having high purity and a high degree of whiteness has been desired. Moreover, from the standpoint of resource and energy savings and pollution control, a process for continuously manufacturing high purity terephthalic acid in good yields over long periods of time has been desired.

For example, in the production of terephthalic acid by the known liquid-phase oxidation of p-xylene, a process for continuous production which comprises feeding p-xylene, a solvent, a catalyst and an oxygen-containing gas continuously into a reactor and meanwhile withdrawing the reaction product continuously from the bottom of the reactor is advantageous over a batchwise process because a product of constant properties can be obtained in a stable manner over long periods of time.

In the manufacture of terephthalic acid using a lower aliphatic carboxylic acid, such as acetic acid as a solvent, the terephthalic acid crystals gradually precipitate in the course of the reaction because terephthalic acid is only sparingly soluble in the aliphatic carboxylic acid solvent, and as a result, crystals adhere to the wall surfaces and other parts of the inside of the reactor. For this reason, it is inevitable in the conventional process that when reaction product builds up in the reactor, the operation should be stopped, and the inside of the reactor thoroughly washed with an aqueous solution of an alkali such as sodium hydroxide to remove the deposited material before the operation is resumed. When this method is used, stopping the operation naturally causes various disadvantages such as a decrease in the rate of operation, variations in the quality of the reaction product, and an increase in the cost of materials and utilities.

An economical and simple process and apparatus for performing the above reaction with good efficiency in which adherence of the aromatic dicarboxylic acid to the walls of the reactor is prevented is not at present known in the art.

When terephthalic acid is produced by feeding p-xylene into a reactor through a single material feed pipe, the product contains various impurities and has poor whiteness. Thus, unless the product is purified, the resulting terephthalic acid does not have a high purity suitable for direct polymerization.

Investigations have now been made into the cause of this difficulty, and it has now been found that when p-xylene is charged through a single feed pipe, the concentration of p-xylene increases locally. It has been confirmed that as a result, an oxidation reaction based on a radical chain mechanism takes place abruptly in areas where the p-xylene concentration is high, and an insufficiency of oxygen occurs in those areas, or a combination of radicals with each other takes place as a side reaction to impede the progress of the desired main reaction. Hence, the resulting terephthalic acid contains increased amounts of coloring products, or includes p-toluic acid and 4-carboxybenzaldehyde which are intermediates in successive reactions which can occur.

In order to obtain high purity terephthalic acid by reducing the amounts of the intermediate products in the above reaction, it is important to disperse the starting material sufficiently in the reactor at the time of charging the starting materials to the reactor, and to oxidize p-xylene to terephthalic acid smoothly and rapidly.

The same can be said with regard to other aromatic dicarboxylic acids as well.

It is known in general chemical reactions to feed a raw material into a reactor through a plurality of nozzles. With this method, however, it is impossible to feed the material uniformly from individual nozzles. In order to attain uniform feeding, a pump or a flow rate controller must be set up for each nozzle, and the apparatus and operation become complicated. Furthermore, the extent of dispersion through a plurality of nozzles is limited. These difficulties render the method extremely disadvantageous both technically and economically.

A method using a single nozzle with a number of pores is also known to improve the dispersion of a raw material without using a number of pumps or flow rate controllers. It has been found that this method produces the intended effect when dispersing the material in a gaseous phase, but that when the material is to be dispersed in a liquid phase as in the present invention, the feed material does not flow uniformly from the individual pores. Furthermore, it has been found that when the nozzle is used in a slurry, the pores become blocked.

SUMMARY OF THE INVENTION

An object of this invention is to provide novel process and apparatus for producing aromatic dicarboxylic acids.

Another object of this invention is to provide a process and an apparatus for producing aromatic dicarboxylic acids without the adhesion and deposition of the aromatic dicarboxylic acids onto the inner walls of a reactor.

Still another object of this invention is to provide a process and an apparatus for producing aromatic dicarboxylic acids of high purity and a high degree of whiteness in high yields.

The present invention in one embodiment provides a process for producing an aromatic dicarboxylic acid by the liquid-phase oxidation of a benzene derivative with oxygen in a lower aliphatic carboxylic acid as a solvent in the presence of an oxidation catalyst, wherein a starting material liquid, i.e., a benzene derivative or a solution of a benzene derivative in the lower aliphatic carboxylic acid as a solvent (hereinafter starting material liquid) is fed into the liquid-phase reaction system in a uniformly dispersed state by being passed through a porous material causing the pressure of the starting material liquid just after passing through said porous material to drop more than about 1 kg/m² in relation to the pressure of the starting material liquid just before passing through said porous material and in another embodiment provides an apparatus or producing the aromatic di-carboxylic acid by the above process, wherein a section for feeding the starting material liquid into the liquid phase of the reactor is composed of the porous material described above.

DETAILED DESCRIPTION OF THE INVENTION

In the process of this invention, the following methods are available in feeding the starting material in a dispersed state into the liquid-phase reaction system through the porous material.

METHOD 1

According to this method, the porous material is used as the wall surface of a reactor. Specifically, in an apparatus for producing aromatic dicarboxylic acids, that part of the reactor which is to contain the liquid-phase reaction mixture comprises a double wall structure comprising an outer wall and an inner wall with the starting material liquid being fed between the outer and inner walls. The inner wall is made up of the porous material so as to prevent the aromatic dicarboxylic acid from adhering and depositing onto the inner wall of the reactor. The feeding of the starting material liquid through this porous material improves the dispersion of the material to an infinite degree, so that an aromatic dicarboxylic acid of high purity can be produced in a stable manner in good yields over long periods of time.

The method is described in detail with reference to the accompanying drawings.

Figure 1:
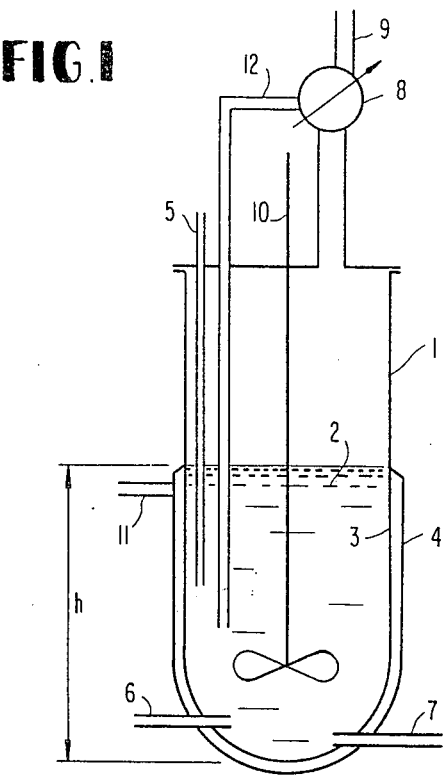
FIGS. 1 and 2 show reactors to which the process of this invention can be applied.

In FIG. 1, the reference numeral 1 represents a reactor; 2, a liquid-phase reaction system; 3, a wall surface made of a porous material; 4, a space between the double wall system; 5, a pipe for feeding a catalyst; 6, a pipe for feeding an oxygen-containing gas such as air; 7, an opening for withdrawal of the product; 8, a vapor condenser; 9, a gas exhaust opening; 10, a stirrer; 11, a pipe for feeding the starting material per se or with a solvent, and 12, a pipe for refluxing condensed liquid. The letter h designates the level or height of the liquid-phase reaction system.

Figure 2:
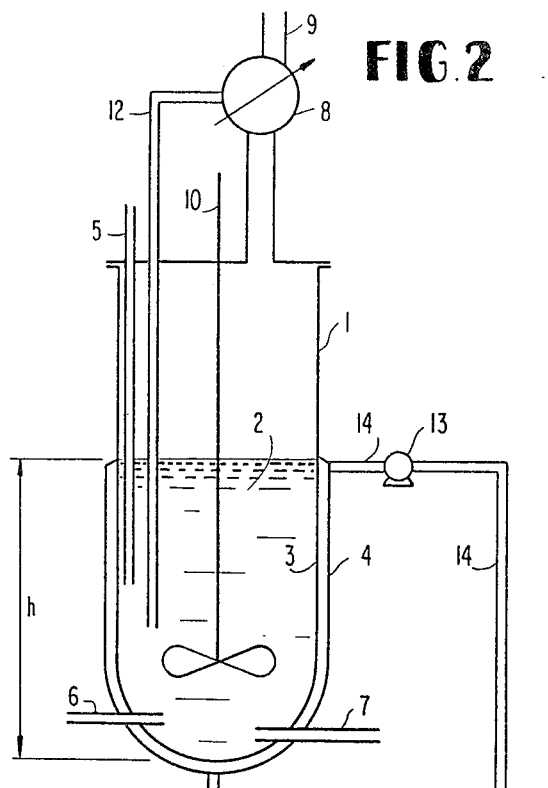

FIG. 2 shows another embodiment of the present invention which is the same as the embodiment shown in FIG. 1 except that it additionally includes a circulating pump 13 for charging the starting material and solvent, a circulating pipe 14, and an external cooling device 15.

Figure 3:
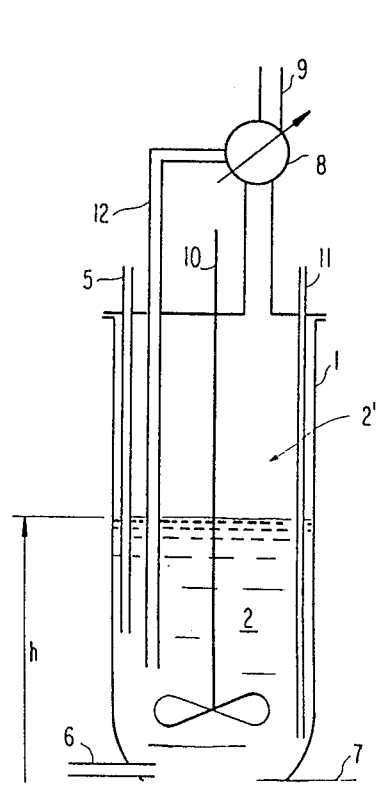
FIG. 3 shows a conventional reaction apparatus.

FIG. 3 is a schematic view showing a reaction apparatus used in Comparative Example 1 given hereinbelow, which differs from the apparatus shown in FIG. 1 in that a gaseous phase of the reaction system is shown at 2', and the wall surface made of a porous material 3 and the space in the double wall system 4 are not employed.

According to the apparatus shown in FIG. 1, the starting material as a liquid or a mixture of the starting material and solvent continuously introduced from the feed pipe 11 enters the space 4 between the double wall system, and is heated as a result of heat exchange with the reaction solution present in the reaction system. Then, it passes through the inner wall 3 made of the porous material and is dispersed as very fine particles in the liquid-phase reaction system 2. Consequently, there is no change in the concentration of the starting material in the liquid-phase reaction system, and good contact and mixing between the starting material and oxygen are maintained, so that the reaction proceeds smoothly.

When the process of this invention is performed in accordance with the embodiment shown in FIG. 2, the wall surface at the part of the reactor contacting the liquid is built as a double wall structure using a porous material. Hence, an additional advantage is obtained in this case over the apparatus shown in FIG. 1 in that the heat generated by the reaction is absorbed by the starting material or the mixture of the starting material and the solvent, and by circulating the liquid through an external cooling device, the heat of reaction can be removed.

Method 1 is especially suitable for a continuous process in which a starting material liquid, a catalyst solution and an oxygen containing gas are continuously fed to the reactor, and the reaction product is continuously withdrawn from the reactor.

The porous material may cover the entire suface of the part of the inner wall of the reactor contacting the liquid phase in the reactor or the portions of the inner wall at which adhesion of the product most readily occurs may be covered by the porous material. Where portions of the inner wall are covered, the porous material employed is preferably distributed in vertical portions of the inner wall contacting the liquid in order to improve the dispersion of the starting material vertically in the reaction liquid.

The reaction apparatus in accordance with this invention provides the following advantages over the conventional apparatus.

(i) Using the above reactor, the starting material is charged equally in a highly dispersed state into the reaction solution through innumerable pores of the porous material making up the inner wall surface of the reactor, and moreover, stirring occurs. The starting material is therefore rapidly dispersed and mixed over the entire area of the reaction system with a uniform concenctiation distribution. Hence, the oxidation reaction proceeds smoothly, while inhibiting side reactions and minimizing a non-uniform reaction and aromatic dicarboxylic acids of high quality can be produced in high yields. Furthermore, with this reaction apparatus it is possible to increase the output of the aromatic dicarboxylic acid to a great extent.

(ii) By feeding the starting material liquid into a reactor through the porous material which makes up the part of the inner wall of the reactor contacting the reaction liquid, the product can be prevented from adhering to the inner wall, particularly at the bottom of the reactor and the vicinity of the opening for passing an oxygen-containing gas into the reactor. This obviates an extra step of stopping the operation and washing away the deposit with an alkali solution which is required in the conventional apparatus. Hence, the oxidation reaction can be continuously performed in a stable manner over long periods of time, and a product of uniform quality and high purity can be obtained in good yields.

(iii) The removal of the heat of reaction is important in a liquid-phase oxidation reaction. When a starting material or a mixture of the starting material and a solvent is fed at a low temperature into a space of a double wall system which forms the part of the inner wall of the reactor contacting the reaction liquid, the starting material or starting material-solvent mixture absorbs the heat of reaction from the reaction mixture, and its temperature is increased to the reaction temperature. It is possible to cool this mixture using an external cooling device thereby removing heat, and then circulate it to the space in the double wall system. Hence, this apparatus has the advantage of removing the heat of reaction. Since the heat of reaction can be removed in a simple manner, the operation becomes easy, and the quality of the product is not only good but also constant. Furthermore, heat recovery can be performed easily.

METHOD 2

According to this method, the porous material is used in a pipe for feeding the starting material liquid. Specifically, in a reaction apparatus for producing aromatic dicarboxylic acids, a part or all of that part of the starting material liquid feed pipe which is within the reaction solution is made of the porous material, so that the starting material fed passes through the porous portion of the starting material feed pipe and is dispersed uniformly in the liquid-phase reaction system.

This method together with the apparatus therefor is described in detail by referring to the accompanying drawings.

Figure 4:
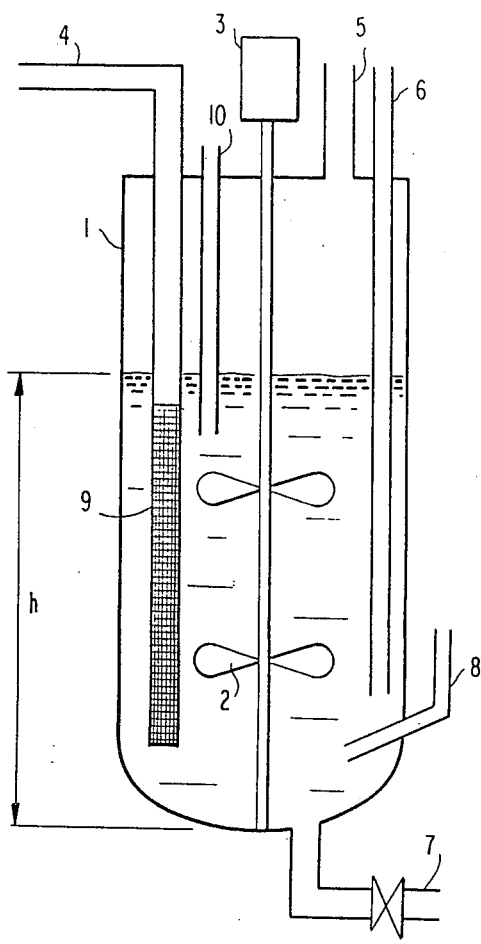
FIGS. 4 and 5 show a reaction apparatus in which the process of this invention can be applied to a material feed pipe.

In FIG. 4, reference numeral 1 represents a reactor; 2, a stirrer; 3, a motor for rotating the stirrer; 4, a starting material liquid feed pipe; 5, a gas exhaust opening; 6, a pipe for refluxing condensed liquid; 7, an opening for withdrawing the reaction product; 8, an opening for introducing an oxygen-containing gas; 9, a porous material; 10, a pipe for feedng a catalyst solution; and h, the level or height of the reaction solution. These reference numerals also apply to FIG. 5.

Figure 5:
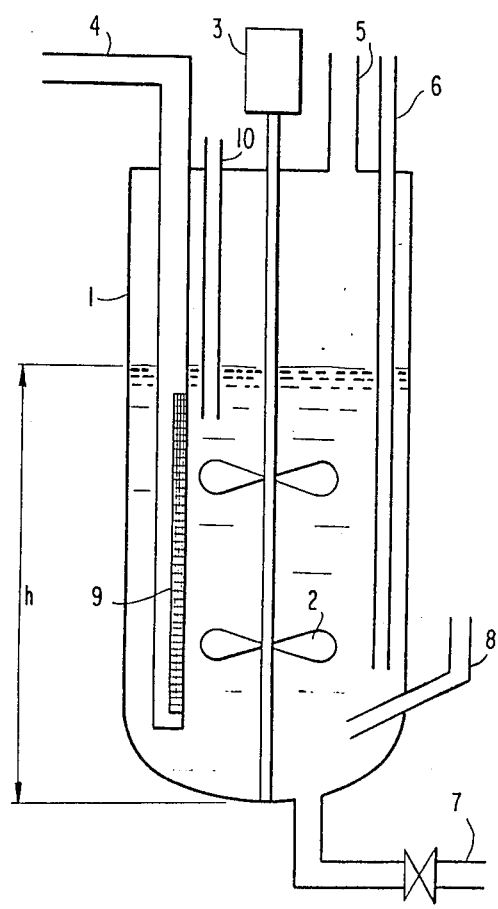

Preferably, the porous material is fitted at a position of the starting material liquid feed pipe which is below the level of the reaction solution and is oriented vertically and parallel to the vertical wall surface of the reactor. The porous material may cover the entire circumference of the starting material liquid feed pipe as shown in FIG. 4, or may cover only a part of the starting material liquid feed pipe as shown in FIG. 5. The porous material may be continuous or discontinuous in the vertical direction of the starting material liquid feed pipe.

This method is suitable both for a continuous process and a semi-continuous process in which a starting material and an oxygen-containing gas are continuously fed into a reactor containing a solvent and a catalyst, and the reaction product is withdrawn from the reactor after the reaction.

According to Method 2 also, the starting material liquid is fed uniformly into the reactor along the vertical direction through an innumerable number of pores in the porous material of the starting material liquid feed pipe, and stirring occurs. Hence, the starting material is rapidly dispersed and mixed over the entire area of the reaction system with a uniform distribution of the concentration, and the oxidation reaction proceeds smoothly. Non-uniform reactions and side reactions can be minimized, and a high purity aromatic dicarboxylic acid with a markedly reduced impurity content and a very high level of whiteness can be produced in good yields. This method also offers a superior economical advantage in that the output of high purity aromatic dicarboxylic acid can be greatly increased.

The process of this invention can be applied to any method of obtaining an aromatic dicarboxylic acid in the liquid-phase oxidation of a benzene derivative with oxygen in a lower aliphatic carboxylic acid as a solvent in the presence of an oxidation catalyst, e.g., as disclosed in U.S. Pat. Nos. 3,361,803, 2,853,517 and 2,833,816.

Saturated fatty acids containing 2 to 8, particularly 2 to 4, carbon atoms in the molecule can be suitably used as the lower aliphatic carboxylic acid. For example, acetic acid, propionic acid and n-butyric acid, especially acetic acid, are generally used with good results.

Suitable catalysts which can be used include salts of heavy metals such as Co, Mn, Ce and Ni (all of which are divalent), especially heavy metal salts of aliphatic carboxylic acids containing 2 to 5 carbon atoms, for example, the acetates, the propionates, and the n-butyrates. Generally, hydrates of these salts are employed. The total amount of the metal component of the heavy metal salt in the reaction system is about 0.01 to about 10% by weight, preferably 0.02 to 5% by weight, based on the solvent.

Bromine, a bromide of a heavy metal as described above, or another bromine-containing compound such as sodium bromide, potassium bromide, hydrobromic acid, bromoform, tetrabromoethane or monobromoacetic acid can be used as a reaction promotor. A suitable amount of such a promotor is such that the weight of the bromine component is about 0.1 to 10 parts by weight, preferably 0.2 to 7 parts by weight, per part by weight of the heavy metal component in the catalyst.

The best results are obtained in this invention with a cobalt/manganese/bromine system catalyst and when the amount of the cobalt component in a cobalt salt is about 0.05 to 0.5% by weight based on the amount of the solvent, the proportion of the manganese component in a manganese salt based on the cobalt component is about 1 to about 20% by weight, the weight ratio of the Br/Co component is about 1.5 to about 6.0, and $CoBr_2$, bromine, or HBr is used as a bromine component.

A cooxidant can also be used in the process of this invention. Examples of suitable cooxidants are aldehydes (e.g., aliphatic aldehydes containing 1 to 4 carbon atoms such as acetaldehyde), ketones (e.g., aliphatic ketones containing 3 to 5 carbon atoms such as dimethyl ketone), and alcohols (e.g., aliphatic alcohols containing 1 to 4 carbon atoms, such as ethyl alcohol; tert-butyl alcohol is not preferred, however since the product quality is deteriorated when such is used). A suitable amount of the cooxidant is about 0.01 to 10 moles, preferably 0.02 to 1 mole, per mole of the benzene derivative used as a starting material.

The catalyst, promotor, and cooxidant are supplied in a conventional manner to the reaction system, and preferably at a flow rate such that the amount of the solution thereof in the above-mentioned proportions in a solvent in the aforementioned ratio is about 0.15 to about 15 times the weight of the starting material benzene derivative.

Examples of aromatic dicarboxylic acids which can be produced by the process and apparatus of this invention can be described by the following formula (I):

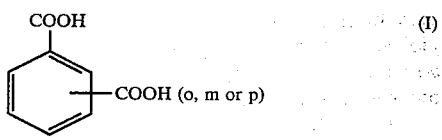

Benzene derivatives of the following formula (II)

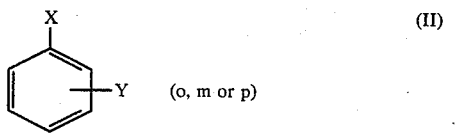

are used as starting materials for the aromatic dicarboxylic acids of the formula (I). In the above formula, X and Y each represents an alkyl group containing 1 to 3 carbon atoms such as methyl, ethyl, isopropyl or propyl, or a haloalkyl group containing 1 to 3 carbon atoms (with suitable halogens being Cl or Br) such as $-CH_2Cl$, $-CH_2Br$, or a formyl group; or one of either X or Y is a carboxyl group.

By using o-, m- and p-xylenes, o-, m- and p-diisopropyl benzenes, o-, m- and p-cymenes, o-, m- and p-diethyl benzenes, and o-, m- and p-tolualdehydes, the corresponding aromatic dicarboxylic acids, that is, phthalic acid, isophthalic acid, and terephthalic acid, can be obtained. The present invention is especially suitable for producing terephthalic acid from p-xylene or p-tolualdehyde.

The oxidation of the starting material is performed in the presence of oxygen (that is, molecular oxygen). Specifically, the oxidation is performed by feeding oxygen gas or an oxygen-containing gas into a solvent solution of the starting material and a catalyst. Any inert gas can be used in admixture with oxygen. Examples of suitable inert gases are helium, neon, argon, and inert gases obtained by burning hydrocarbons (for example, when a mixture of butane and air in a stoichiometric amount or in a larger amount (usually, 30 $NM^3$ of air per 1 $NM^3$ of butane) is burned at room temperature (e.g., 20°–30° C.) or at a temperature slightly higher than room temperature, a mixture of 87% by volume of $N_2$, 10% by volume of $CO_2$, less than 2.0% by volume of $O_2$, and less than 1.0% by volume of CO can be obtained if the ratio of butane to air is as indicated above). For practical purposes, air is used. A mixture of air with another inert gas e.g. as described above, or an exhaust gas from the reactor whose oxygen concentration has been supplemented by adding oxygen or air thereto can also be used. The amount of oxygen in the oxygen-containing gas is generally at least about 10% by volume. Although larger amounts of oxygen are better, the oxygen content and the rate of feeding oxygen are generally so determined that the amount of oxygen in the exhaust gas is less than about 8% by volume, in order to eliminate the danger of explosion.

A suitable amount of the lower aliphatic carboxylic solvent in the reaction system is about 1 to about 35 times, preferably 1.5 to 15 times, the weight of the benzene derivative starting material. The starting material benzene derivative may be fed alone or as a solution in the above solvent in a concentration of about 2 to about 50% by weight or even higher. If the capacity of the reactor is v, then the rate of feeding the starting material is about 0.001 v/hr to about 10 v/hr, preferably 0.01 v/hr to 5 v/hr. If the rate of feeding is less than about 0.001 v/hr, a large-sized reactor is required if output beyond a certain limit is desired. This is economically disadvantageous. On the other hand, if the rate exceeds about 10 v/hr, the reaction time is insufficient, and the amounts of intermediate reaction products increase.

The pressure at the time of the reaction is a pressure sufficient to maintain the reaction system liquid. Usually, a suitable pressure is about 1 to about 70 atmospheres, preferably 5 to 50 atmospheres.

A suitable reaction temperature is about 100° to about 250° C., preferably 180° to 220° C. The higher the reaction temperature is, the faster is the rate of reaction. Hence, the diffusion step, such as the step of dispersing the starting material is the step controlling the rate of reaction. Thus, according to the process of this invention in which diffusion of the starting material to an extremely high degree can be achieved, the output per unit time can be improved by increasing the reaction temperature. The process of this invention is especially effective when the reaction temperature is about 180° to about 220° C.

Shorter reaction periods are preferred in this invention. However, from the stand point of the yield of the reaction product and economy, the reaction time is generally about 0.1 to about 10 hours, preferably 0.5 to 5 hours.

The slurry-like reaction product removed from the reactor, after being subjected, if desired, to a crystallization treatment in a conventional manner, is cooled to room temperature and then subjected to a conventional solid-liquid separation using, for example, a centrifugal separator or a decanter to separate the reaction product from the mother liquor. The resulting aromatic dicarboxylic acid is washed with a solvent e.g., a lower aliphatic acid, e.g., acetic acid, propionic acid, butyric acid, etc., such as that used as the reaction solvent, and dried. The catalyst is recovered, and recycled for reuse.

Exemplary but non-limiting materials which can be used as the porous material in this invention are ceramic materials, vitreous materials, carbon, graphite, and metals such as titanium, carbon steel, stainless steel, zirconium or tantalum. Although any material which is inert to the reaction and maintained porous can be used, the above-cited materials are particularly suitable.

The metal can be used in the form of a gauze. Furthermore, the metal can be used as a sintered metal by compressing particles of the metal (with an average particle diameter of about 0.05 to 0.5 mm) with or without heating. The pressure and temperature for sintering can be varied as needed depending, for example, on the kind of the metal, the shape of the pores, or the thickness of the molded article. For example, by molding a titanium powder with a particle diameter of 0.25 to 0.35 mm at a temperature of 800° C. under a pressure of 0.6 to 1.2 tons/cm$^2$, a sintered product having a pore size of 36 to 63 microns can be obtained. Those having a thickness of about 2 to 6 mm are desirable for use in the process of this invention.

When a ceramic material is used as the porous material, a material such as silica sand, alumina, or chamotte (aluminum silicate) having an average particle diameter of about 0.1 to 0.7 mm is calcined together with about 0.1 to about 10% by weight of a binder such as a glass, an α-alumina, etc., at a temperature of about 1300° to about 2000° C.

When a vitreous material is used as a porous material, a material having a particle diameter of about 0.1 to about 0.5 mm is molded together with about 0.1 to about 10% by weight of a binder e.g., sodium silicate, and calcined at about 800° to about 1500° C. An example of such a material is sintered glass.

When carbon or graphite is used as a porous material, it is prepared by adding about 0.1 to about 10% by weight of a binder composed of pitch adjusted with tar to render such fluid to petroleum coke pulverized to a particle diameter of about 0.01 to 1 mm, mixing and kneading the mixture while heating the mixture at a temperature of about 30° to about 100° C., molding the mixture, and calcining the mixture at about 1000° to about 1200° C. or graphatizing the mixture at about 2300° to about 2700° C. (that is, growing crystals of graphite at high temperatures), followed by relatively increasing the size of the remaining pores or rendering the sizes of the pores uniform.

A suitable porosity for the porous material used in this invention is usually about 10 to about 70%, preferably 20 to 60% according to JIS Z-2506. Briefly in this method, the sample of the porous material is dried and the weight is measured. The sample is placed in a vessel at a pressure of 30 mmHg and allowed to stand for 30 min. An oil (kinematic viscosity: 29.0±5.0 centistokes at 50° C.) heated to 80° C. is charged into the vessel until the sample is completely immersed and the sample is allowed to stand for 30 min. in a vacuum. After returning the pressure in the vessel to normal pressure and cooling to room temperature, the sample is removed and the weight thereof is measured. Then, the sample containing the oil is immersed in water and the weight thereof in water is measured. The porosity is calculated from the following relationship.

$$P = \frac{B - A}{(B - C) \times S} \times 100$$

wherein
P: Effective pore percentage by volume
A: Weight of sample containing no oil (g)
B: Weight of sample containing oil (g)
C: Weight of sample containing oil in water (g)
S: Specific gravity of oil at the test temperature If the porosity is less than about 10%, the dispersing effect of the porous material is small because the dispersion becomes low. On the other hand, porosities exceeding 70% decrease the strength of the porous material.

The average porosity of the porous material depends upon the flow rate of the material passing through the porous material.

A suitable pore diameter of the porous material is generally about 1 to about 1000μ, preferably 1 to 500μ, more preferably 2 to 100μ, when the porous material is used in the wall surface of a reactor, and is about 1 to about 1,000μ, preferably 2 to 500μ, more preferably 20 to 500μ, when the porous material is used in the wall surface of a starting material feed pipe. In either case, the effect of dispersing the starting material liquid is reduced if the pore diameter exceeds the upper limit specified. Furthermore, in either case, when the pore diameter is smaller than the lower limit, the load (discharge head pressure) of the pump used for feeding the starting material liquid is extremely high resulting in economic disadvantages. Generally, the thickness of the porous material is about 1 to 50 mm, and is determined taking into consideration the mechanical strength of the porous material.

A suitable flow rate of the starting material liquid passing through the porous material is about $10^{-5}$ to about $10^2$ liters/hr/cm$^2$. If the flow rate is below about $10^{-5}$ liter/hr/cm$^2$, the starting material liquid does not flow uniformly through all of the pores of the porous material. On the other hand, if the flow rate is larger than about $10^2$ liter/hr/cm$^2$, the pressure drop is great, and the load of a pump used for feeding the starting material is increased.

As described above, it is desirable to use the porous material having a limited porosity, pore size, thickness, etc., but it is necessary in the present invention that the porous material contains pores providing a pressure drop above about 1 kg/m$^2$, as described above, calculated based on the Carman-Kozeny equation (*Manual of Chemical Engineering*, page 134 (1968), published by Maruzen Company Limited (Japan)).

The process of this invention is especially advantageous when it is desired to increase the output of the final product. When the process of this invention is applied to a reactor of a specific capacity, the output of the product can be increased without reducing the quality of the product because the process of this invention ensures good dispersion of the starting material. In the conventional process, when the amount of the starting material to be supplied to the reactor is increased, the amount of the product deposited onto the reactor increases. This problem can be obviated by the process of this invention.

Some of the effects of the present invention are illustrated by reference to the following Examples and Comparative Examples which are not in any way to be construed as limiting the scope of the invention. All parts in the examples are by weight unless otherwise specified.

EXAMPLE 1

In a reaction chamber having a diameter of 240 mm and a height of 850 mm as shown in FIG. 1, a pipe (270 mm) for feeding a catalyst solution, an opening for feeding air, an opening for withdrawal of the product, a gas exhaust opening and a stirrer (200 rpm) were provided. The entire inner wall surface of the part of the reaction chamber contacting liquid was built of a porous sintered titanium material to form a double wall structure. The reactor was charged with 100 parts of acetic acid, 0.6 part of cobalt acetate, 0.03 part of manganese acetate, and 0.3 part of sodium bromide, p-xylene was fed into the reactor at a flow rate of 4.0 kg/hr 210° C. and 20 kg/cm$^2$, and air was fed at a rate of 20 NM$^3$/hr for 30 minutes into the reactor. The pressure and temperature of the reaction system were 20 kg/cm$^2$, and 210° C., respectively.

Then, while feeding air at the same rate, a mixture of p-xylene and acetic acid, as a solvent, in a weight ratio of 1:2 was fed into a space 4 of the double wall system at a rate of 12.0 kg/hr, and passed through the wall surface 3 of the porous material. Further a catalyst-acetic acid solution was charged at a rate of 4.0 kg/hr (the concentration of the catalyst was three times that of the catalyst initially charged). In the meantime, reaction product was withdrawn so as to maintain the liquid level of the reaction chamber constant. The average residence time of the reaction solution was 1 hour. In this way, the operation was performed continuously for 500 hours. The properties of terephthalic acid sampled during the operation are shown in Table 1 below.

After the reaction, the reactor was opened, and it was found that the product did not adhere to the reactor wall, nor were the pores of the porous material blocked. The yield of the product was 96%, and the quality of the product was very good.

In this example, the porous material was made of sintered titanium metal and had an average pore diameter of 40μ, a porosity of 30% and a thickness of 5 mm the porous material covered the entire wall surface of the liquid-contacting portion as shown in FIG. 1. The height of the reaction solution (h) was 450 mm. The pressure drop caused by the porous material used was 4 kg/m².

EXAMPLE 2

The same reactor as described in Example 1 was used, and the double wall structure of the reactor was so designed that the starting material solution was circulated through a cooling device 15 provided outside the reactor, as shown in FIG. 2. A 1:2 (by weight) mixture of p-xylene and acetic acid was circulated through this system. The amount of the mixture circulated was 5 times the weight of the mixture charged into the reactor through the porous material.

The reaction was performed under the same conditions as in Example 1 at a temperature of 190° C. and a pressure of 24 kg/cm². Since an exterior cooling device was provided, the reaction pressure used could be higher than in Example 1. In this way, the operation was performed continuously for 500 hours. The properties of terephthalic acid sampled during the operation are shown in Table 1. When the reactor was opened after the reaction, scarcely no deposition of terephthalic acid onto the reactor wall was observed, and the yield and quality of terephthalic acid were extremely good.

When Example 2 is compared with Example 1, it can be seen that by circulating a mixture of p-xylene and acetic acid solvent the reaction pressure can be increased from 20 kg/cm² to 24 kg/cm², and this evidently increased the quality of the product. The yield of the product was 96%.

EXAMPLE 3

The procedure in Example 1 was repeated except that p-diethylbenzene was used as the starting material, and the reaction was carried out at 150° C. and 10 kg/cm². The operation was performed continuously, and after a steady state was reached, the product was sampled and analyzed. The results obtained are shown in Table 1 below. The yield of the product was 96%.

COMPARATIVE EXAMPLE 1

The same reaction as in Example 1 was performed except that a reactor with a diameter of 240 mm and a height of 850 mm which was equipped with a starting material feed pipe, a pipe for feeding a catalyst solution, an opening for feeding air, an opening for withdrawing the product, a vapor condenser, an exhaust gas opening and a stirrer as shown in FIG. 3 was used, and a 1:2 (by weight) mixture of p-xylene and acetic acid was fed from a single material feed pipe 4. The results obtained are shown in Table 1 below. The yield of the product was 92%.

TABLE 1

Properties of terephthalic acid

| Reaction Time (hrs.) | Item Analyzed | Example 1 | Example 2 | Example 3 | Comparative Example 1 |
|---|---|---|---|---|---|
| 10 | Purity (wt. %) | 99.97 | 99.97 | 99.95 | 99.94 |
|  | 4-CBA (*1) (ppm) | 300 | 290 | 430 | 460 |
|  | MEC (*2) (380 mμ) | 0.03 | 0.02 | 0.06 | 0.06 |
|  | Color difference, b value (*3) | 1.5 | 0.8 | 2.8 | 3.6 |
| 20 | Purity (wt. %) | 99.97 | 99.97 | 99.95 | 99.94 |
|  | 4-CBA (ppm) | 300 | 300 | 440 | 520 |
|  | MEC (380 mμ) | 0.03 | 0.02 | 0.06 | 0.08 |
|  | Color difference, b value | 1.5 | 0.8 | 2.8 | 4.3 |
| 50 | Purity (wt. %) | 99.97 | 99.97 | 99.95 | 99.5 |
|  | 4-CBA (ppm) | 310 | 300 | 440 | 790 |
|  | MEC (380 mμ) | 0.03 | 0.02 | 0.06 | 0.29 |
|  | Color difference, b value | 1.6 | 0.8 | 2.8 | 11.8 |
| 100 | Purity (wt. %) | 99.96 | 99.97 | 99.95 | — |
|  | 4-CBA (ppm) | 310 | 300 | 440 | — |
|  | MEC (380 mμ) | 0.03 | 0.02 | 0.07 | — |
|  | Color difference, b value | 1.6 | 0.8 | 2.8 | — |
| 300 | Purity (wt. %) | 99.96 | 99.96 | 99.95 | — |
|  | 4-CBA (ppm) | 330 | 320 | 440 | — |
|  | MEC (380 mμ) | 0.03 | 0.02 | 0.07 | — |
|  | Color difference, b value | 1.6 | 0.9 | 2.8 | — |
| 500 | Purity (wt. %) | 99.96 | 99.96 | 99.95 | — |
|  | 4-CBA (ppm) | 340 | 330 | 440 | — |
|  | MEC (380 mμ) | 0.03 | 0.02 | 0.07 | — |
|  | Color difference, b value | 1.7 | 0.9 | 2.9 | — |

Note
(*1) 4-CBA = 4-carboxybenzaldehyde
(*2) MEC stands for molecular extinction coefficient, and such was determined as follows:
5 g of terephthalic acid was dissolved in 100 ml of a 2N aqueous solution of ammonia, and the absorption of the solution at 380 mμ was measured using a spectrophotometer. Smaller numbers indicate better color hues.
(*3) The b value shows the color of the external color or appearance, and was determined by measuring the reflected light of solid terephthalic acid using a color difference meter (Model CM-20 supplied by Color Machine Co., Ltd.). Smaller b values show better color hues.

It can be seen from the results in Table 1 that according to the process of this invention, a high purity product having a good color hue can be obtained in a stable manner over a long period of time, whereas in Comparative Example 1 in which the process of this invention was not involved the product had poor purity and color hue, and the quality and color deteriorated with the passage of time.

EXAMPLE 4

A reactor of the type shown in FIG. 4 including a reaction chamber having an inside diameter of 240 mm and a height of 850 mm and equipped with a starting material feed pipe, a pipe for charging a catalyst solution, a pipe for feeding an oxygen-containing gas, an opening for withdrawing the reaction product, a gas exhaust opening, a pipe for refluxing the condensed liquid and a stirrer (180 rpm) was charged with 100 parts of acetic acid, 0.6 part of cobalt acetate, 0.03 part of manganese acetate, and 0.3 part of sodium bromide. p-Xylene and air were fed for 30 minutes at a rate of 4.0 kg/hr, and 20 NM$^3$/hr at 20 kg/cm$^2$ and 210° C., respectively. Then, while feeding air and p-xylene under these conditions, a catalyst-acetic acid solution was fed at a rate of 12.0 kg/hr (the concentration of the catalyst was the same as that in the initially charged feed). In the meantime, the reaction product was withdrawn so as to maintain the level of the reaction solution constant (at a height of 450 mm). The operation was continuously performed in this way. When a steady state was reached, the product was sampled, and analyzed. The results obtained are shown in Table 2 below.

A porous material (thickness 3 mm) composed of sintered titanium with an average pore diameter of 20$\mu$ and a porosity of 30% was set in the material feed pipe as shown in FIG. 4 (the length of the porous portion was 20 cm; the porous portion constituted the entire peripheral wall of the pipe; the outside diameter was 14 mm; pressure drop caused: 150 kg/m$^2$).

The results shown in Table 2 demonstrate that the 4 carboxybenzaldehyde content, molecular extinction coefficient, color difference and yield of the resulting terephthalic acid were far superior to those of the product obtained in Comparative Example 2 below, and the effect of the reaction apparatus in accordance with the present invention can be clearly seen.

EXAMPLE 5 p-Xylene was oxidized under the same conditions as in Example 4 except that a reactor of starting type shown in FIG. 5 was used in which the porous portion of the material feed pipe was made of a ceramic porous material having an average pore diameter of 40$\mu$ and a porosity of 40% (a cylindrical ceramic filtering material having a thickness of 3 mm was fitted into a pipe with an inside diameter of 16 mm of which 30% of the peripheral wall thereof had been cut away in the longitudinal direction); a 1:1 (by weight) mixture of p-xylene and acetic acid was charged into the reactor through the material feed pipe at a rate of 8.0 kg/hr; and a catalyst-/acetic acid solution was charged at a rate of 8.0 kg/hr (the concentration of the catalyst was ⅔ of the catalyst-/acetic acid solution in Example 4).

The results obtained are shown in Table 2 below.

EXAMPLE 6

The procedures in Example 4 were repeated except that p-diisopropylbenzene was used as the starting material, and fed into the reactor at 150° C. and 10 kg/cm$^2$. (Since the rate of reaction of p-diisopropylbenzene is high, good results can be obtained even at this relatively low temperature.)

The operation was performed continuously in this way, when a steady state was reached, the product was sampled, and analyzed. The results obtained are shown in Table 2 below.

COMPARATIVE EXAMPLE 2

The procedures in Example 4 were repeated except that titanium metal having an average pore diameter of 1200$\mu$, a porosity of 15% and a thickness of 3 mm was used as the porous material for the starting material liquid feed pipe. The results obtained are shown in Table 2 below.

This Comparative Example is an example where the average pore size is outside the preferred range and the pressure drop caused is 0.5 kg/m$^2$ which is outside the range recited of the present invention.

TABLE 2

| Item Analyzed | Example 4 | Example 5 | Example 6 | Comparative Example 2 |
|---|---|---|---|---|
| Purity (wt. %) | 99.97 | 99.97 | 99.95 | 99.94 |
| 4-Carboxybenzaldehyde content (ppm) | 310 | 330 | 450 | 470 |
| Molecular extinction coefficient (at 380 m$\mu$) | 0.04 | 0.05 | 0.03 | 0.07 |
| Color difference, b-value | 2.0 | 2.1 | 1.6 | 3.5 |
| Yield (mole %) | 96 | 96 | 95 | 92 |

As can be seen from the results obtained, the quality and yield of the resulting terephthalic acid in Example 4 were better than in Comparative Examples 1 and 2, and the effect of the present invention in using a porous material in the starting material feed pipe can be markedly observed.

In order to compare the apparatus used in Example 4 with that used in Example 5, the amount of p-xylene supplied through the starting material feed pipe was increased. However, hardly any change in the quality and yield of the resulting terephthalic acid was observed.

It is clear therefore that by using the reaction apparatus of this invention which uses a porous material in the material feed pipe, the output of terephthalic acid of high purity increases greatly.

EXAMPLE 7

The procedures of Example 1 were repeated except that m-xylene was used instead of p-xylene. Isophthalic acid was obtained, and the results were as good as in the case of using p-xylene.

EXAMPLE 8

The procedures of Example 5 were repeated except that m-xylene was used instead of p-xylene. Isophthalic acid was obtained, and the results were as good as in the case of using p-xylene.

EXAMPLE 9

The procedures of Example 1 were repeated except that p-tolualdehyde was used instead of p-xylene. Terephthalic acid was obtained, and the results were as good as in Example 1.

When the same procedures as above were repeated except that other benzene derivatives were used as the starting material, substantially the same results as in Examples 1 to 9 were obtained.

While the invention has been described in detail and with reference to specific embodiments thereof, it will be apparent to one skilled in the art that various changes and modifications can be made therein without departing from the spirit and scope thereof.

What is claimed is:

1. In a process for producing an aromatic dicarboxylic acid by liquid-phase oxidation of a benzene derivative with molecular oxygen in a lower aliphatic carboxylic acid as a solvent in the presence of an oxidation catalyst, the improvement comprising feeding a starting material liquid comprising said benzene derivative or a solution of said benzene derivative in said solvent in a uniformly dispersed state into the liquid-phase reaction system by passing said starting material liquid through a porous material causing the pressure of the starting material liquid just after passing through said porous material to drop more than about 1 kg/m² in relation to the pressure of the starting material liquid just before passing through said porous material.

2. The process of claim 1, wherein a reactor having a double wall structure comprising an outer wall and an inner wall at least a part of which is made of a porous material is used, and said process includes feeding said starting material liquid into a space between the outer wall and the inner wall, and charging said starting material liquid into the liquid-phase reaction system through the porous material.

3. The process of claim 1, wherein a reaction apparatus having a material feed pipe a portion of which present in the liquid-phase reaction system at least partly comprises a porous material is used, and said process includes feeding said starting material liquid into the liquid-phase reaction system through the porous material.

4. The process of claim 1, wherein the benzene derivative has the general formula (I)

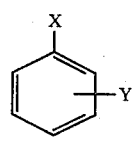

(I)

wherein X and Y each represents an alkyl group containing 1 to 3 carbon atoms, a haloalkyl group containing 1 to 3 carbon atoms, or a formyl group, or either of X or Y represents a carboxyl group and wherein Y can be in the ortho-, meta- or para-position of said ring to X.

5. The process of claim 1, wherein the benzene derivative is o-, m- or p-xylene, o-, m- or p-diisopropyl benzene, o-, m- or p-cymene, o-, m- or p-diethyl benzene, or o-, m- or p-tolualdehyde, and phthalic acid, isophthalic acid or terephthalic acid is produce depending on the o-, m- or p-positioning of the benzene derivative used.

6. The process of claim 1, wherein the oxidation catalyst is a salt of cobalt, manganese, cerium or nickel with an aliphatic carboxylic acid having 2 to 5 carbon atoms.

7. The process of claim 1, wherein the reacting is additionally in the presence of a promotor selected from the group consisting of bromine, a bromide of cobalt, manganese, cerium or nickel, hydrobromic acid, sodium bromide, potassium bromide, bromoform, tetrabromoethane, and monobromoethane.

8. The process of claim 1, wherein the reacting is at a temperature of about 100° to about 250° C. and at a pressure which is sufficient to maintain the reaction system liquid.

9. The process of claim 1, wherein the porous material is a porous material made of a ceramic material, a vitreous material, carbon, graphite, titanium, carbon steel, stainless steel, zirconium or tantalum.

10. The process of claim 1, wherein the porous material has a porosity of about 10 to about 70%.

11. The process of claim 1, wherein the porous material has a pore size of about 1 to about 1,000μ.

12. The process of claim 1, wherein the porous material has a thickness of 1 to 50 mm.

13. The process of claim 2, including absorbing the heat of reaction by feeding said starting material liquid into the space between the outer wall and the inner wall, and recycling a part of the starting material liquid thereof to the reactor through an exterior cooling device.

14. The process of claim 1, wherein the flow rate of the starting material liquid passing through the porous material is about $10^{-5}$ to about $10^2$ liters/hr/cm².

15. The process of claim 1 wherein the porous material has a porosity of about 10 to 70%.

16. The process of claim 1 wherein the porous material has a pore size of about 1 to about 1,000μ.

17. The process of claim 1 wherein the porous material is about 1 to about 50 mm thick.

18. In a process for producing an aromatic dicarboxylic acid by the liquid-phase oxidation of a benzene derivative with molecular oxygen in a lower aliphatic carboxylic acid solvent in the presence of an oxidation catalyst by means of a vertically oriented generally cylindrical reactor capable of retaining a liquid therein, in which said reactor has (a) means for feeding liquid starting material to the liquid phase in said reactor, said means for feeding liquid starting material comprising a tubular member being oriented vertically in the liquid phase in said reactor; (b) means in said reactor for stirring the liquid phase in said reactor; (c) means for passing molecular oxygen or molecular oxygen containing gas into the liquid phase in said reactor; (d) means for feeding an oxidation catalyst into said reactor; (e) means for removing the product from the bottom of said reactor; and (f) means for recovering the vapor from the upper portion of said reactor; introducing the vapor into the condenser, and refluxing the resulting condensate into said reactor, characterized in that the liquid phase portion of said tubular member for feeding liquid starting material to the liquid phase in said reactor at least partially comprises a porous material, the porous material is oriented vertically in the liquid phase, the liquid starting material is fed into the liquid phase of said reactor through the porous material of said tubular member, the pressure of said liquid starting material drops by more than 1 kg/m² during passage through said porous material and the liquid starting material is fed into the liquid-phase reaction system in a dispersed state.

19. The process of claim 18, wherein the liquid starting material is a benzene derivative or a mixture of the benzene derivative and a lower aliphatic carboxylic acid solvent.

20. The process of claim 18, wherein the oxidation catalyst is fed to said reactor dissolved in a lower aliphatic carboxylic acid.

21. The process of claim 18 wherein the porous material is made of a ceramic material, a vitreous material, carbon, graphite, titanium, carbon steel, stainless steel, zirconium or tantalum.

22. The process of claim 18, wherein the benzene derivative has the general formula (I)

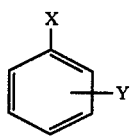

wherein X and Y each represents an alkyl group containing 1 to 3 carbon atoms, a haloalkyl group containing 1 to 3 carbon atoms, or a formyl group, or either of X or Y represents a carboxyl group and wherein Y can be in the ortho-, meta- or para-position of said ring to X.

23. The process of claim 18, wherein the benzene derivative is o-, m- or p-xylene, o-, m- or p-diisopropyl benzene, o-, m- or p-cymene, o-, m- or p-diethyl benzene, or o-, m- or p-tolualdehyde; and phthalic acid, isophthalic acid or terephthalic acid is produced depending on the o-, m- or p-positioning of the benzene derivative used.

24. The process of claim 18, wherein the oxidation catalyst is a salt of cobalt, manganese, cerium or nickel with an aliphatic carboxylic acid having 2 to 5 carbon atoms.

25. The process of claim 18, wherein the reacting is additionally in the presence of a promotor selected from the group consisting of bromine, a bromide of cobalt, manganese, cerium or nickel, hydrobromic acid, sodium bromide, potassium bromide, bromoform, tetrabromoethane, and monobromoethane.

26. The process of claim 18, wherein the reacting is at a temperature of about 100° to about 250° C. and at a pressure which is sufficient to maintain the reaction system liquid.

27. The process of claim 18, wherein the porous material is a porous material made of a ceramic material, a vitreous material, carbon, graphite, titanium, carbon steel, stainless steel, zirconium or tantalum.

28. The process of claim 18, wherein the porous material has a porosity of about 10 to about 70%.

29. The process of claim 18, wherein the porous material has a pore size of about 1 to about 1,000μ.

30. The process of claim 18, wherein the porous material has a thickness of 1 to 50 mm.

31. The process of claim 18, wherein the flow rate of the starting material liquid passing through the porous material is about $10^{-5}$ to about $10^2$ liters/hr/cm².

* * * * *